United States Patent [19]

White et al.

[11] Patent Number: 5,804,367
[45] Date of Patent: *Sep. 8, 1998

[54] METHOD FOR QUANTIFYING LBP IN BODY FLUIDS

[75] Inventors: Mark Leslie White, Sonoma; Stephen Fitzhugh Carroll, Walnut Creek; Jeremy Kam-kuen Ma, San Ramon, all of Calif.

[73] Assignee: Xoma Corporation, Berkeley, Calif.

[*] Notice: The term of this patent shall not extend beyond the expiration date of Pat. No. 5,484,705.

[21] Appl. No.: 377,391

[22] Filed: Jan. 24, 1995

Related U.S. Application Data

[63] Continuation-in-part of Ser. No. 186,811, Jan. 24, 1994, Pat. No. 5,484,705.

[51] Int. Cl.⁶ .................. G01N 33/566; G01N 33/569; C12Q 1/00
[52] U.S. Cl. .................. 435/4; 435/7.1; 435/7.32; 435/7.5; 435/7.92; 435/7.94; 435/7.95; 435/7.9; 436/501; 436/811
[58] Field of Search .................. 435/7.1, 7.32, 435/7.9, 7.94, 7.95, 4, 7.5, 7.92; 436/501, 518, 811

[56] References Cited

U.S. PATENT DOCUMENTS

| 5,245,013 | 9/1993 | Ulevitch et al. |
| 5,310,879 | 5/1994 | Ulevitch . |
| 5,484,705 | 1/1996 | White . |

FOREIGN PATENT DOCUMENTS

| WO 91/01639 | 2/1991 | WIPO . |
| WO 93/06228 | 4/1993 | WIPO . |
| WO 94/21280 | 9/1994 | WIPO . |
| WO 94/25476 | 11/1994 | WIPO . |
| WO 95/00641 | 1/1995 | WIPO . |
| WO 95/02414 | 1/1995 | WIPO . |

OTHER PUBLICATIONS

Ulevitch, Presentation at the American Society of Microbiology General Meeting in Atlanta, Georgia (May 16–21, 1993) (Session 13 Abstract 564).

Tobias et al., "Lipopolysaccharide Binding Protein" *J. Cell. Biochem.*, 16 C:151 (Abstract (CB006) (1992).

Ballou et al., "Laboratory Evaluation of Inflammation," *Textbook of Rheumatology*, vol. 1, Ch. 40, pp. 671–679 (1993).

Baumann et al., "The acute phase response," *Immunology Today*, vol. 15, 1/4 1/2. 2, pp. 74–80 (1994).

Grube et al., "Lipopolysaccharide Binding Protein Expression in Primary Human Hepatocytes and HepG2 Hepatoma Cells*," *J. Biol. Chem.*, vol. 269, No. 11, pp. 8477–8482 (1994).

Raynes, "Carbohydrate Binding Proteins and Immune Responses," Biochemical Immunology Group/Glycobiology Group Joint Colloquium Organized by G.B. Wisdom and M.I. Halliday (The Queen's University, Belfast) and Edited by G.B. Wisdom. 648th Meeting held at the Queen's University, Belfast, 14–17 Sep. 1993, *Biochemical Society Transactions*, vol. 22, pp. 69–74 (1994).

Meszaros et al., "Immunoreactivity and Bioactivity of Lipopolysaccharide–Binding Protein in Normal and Heat–Inactivated Sers," *Infection and Immunity*, vol. 63, No. 1, pp. 363–366 (1995).

Pugin et al., "Soluble CD14 and Lipopolysacchardie Binding Protein Mediate Epithlial Cell Responses to Lipopolysaccharides," *FASEB J.*, A142 (1993).

Geller et al *Arch Surg*, 128: 22–28, 1993 (Jan. 22).

Tobias *J.Biol. Chem* 263:13479–13481, 1988.

Dofferhoff et al., "Tumor necrosis factor (cachectin) and other cytokines in septic shock: a review of the literature", *Netherlands J. Med.*,39:45–62 (1991).

Elsbach et al., "Separation and Purification of a Potent Bactericidal/Permeability–increasing Protein and a Closely Associated Phospholipase $A_2$ from Rabbit Polymorphonuclear Leukocytes", *J. Biol. Chem.*, 254(21):11000–11009 (Nov. 10, 1979).

Erwin and Munford, "Plasma Lipopolysaccharide–Deacylating Activity (Acyloxyacyl Hydrolase) Increases After Lipopolysaccharide Administration to Rabbits", *Lab. Invest.*, 65(2):138–144 (1991).

Gallay et al., "Purification and Characterization of Murine Lipopolysaccharide–Binding Protein", *Infect. Immun.* 61(2):378–383 (Feb. 1993).

Gazzano–Santoro et al., "High–Affinity Binding of the Bactericidal/Permeability–Increasing Protein and a Recombinant Amino–Terminal Fragment to the Lipid A Region of Lipopolysaccharide", *Infect. Immun.* 60(11):4754–4761 (Nov. 1992).

Leturcq et al, "Generation of Monoclonal Antibodies to Human LBP and Their Use in the Detection of LBP Protein in Serum", *J. Cell. Biochem.*, 16C:161 (1992).

Marra et al., "The Role of Bactericidal/Permeability–Increasing Protein as a Natural Inhibitor of Bacterial Endotoxin", *J. Immun.*, 148(2):532–537 (Jan. 15, 1992).

Pereira et al, "Quantitation of a cationic antimicrobial granule protein of human polymorphonuclear leukocytes by ELISA", *J. Immunol. Methods*, 117:115–120 (1989).

Pesce et al., "Cationic antigens Problems associated with measurement by ELISA", *J. Immunol. Methods*, 87:21–27 (1986).

(List continued on next page.)

*Primary Examiner*—Paula K. Hutzell
*Assistant Examiner*—Nancy A. Johnson
*Attorney, Agent, or Firm*—Marshall, O'Toole, Gerstein, Murray & Borun

[57] ABSTRACT

The present invention provides a method for quantifying the presence of extracellular LBP in body fluids including blood in a subject comprising conducting an LBP immunoassay on plasma obtained from said subject.

11 Claims, 5 Drawing Sheets

OTHER PUBLICATIONS

Schindler et al., "Plasma levels of bactericidal/permeability–increasing protein (BPI) and lipopolysaccharide–binding protein (LBP) during hemodialysis", *Clin. Nephrology,* 40(6):346–351 (1993).

Schumann et al., "Structure and Function of Lipopolysaccharide Binding Protein", *Science,* 249:1429–1433 (Sep. 21, 1990).

Spitznzgel, "Antibiotic Proteins of Human Neutrophilia", *J. Clin. Invest.,* 86:1381–1386 (1990).

Taber et al., Taber's Cyclopedic Medical Dictionary, p. 545 (F.A. David Co., Philadelphia) (1985).

Ulevitch, Presentation at the merican Society of Microbiology General Meeting in Atlanta, Georgia (May 16–21, 1993).

von der Mohien et al., Bactericidal/Permeability–Increasing Protein Levels Predict Survival in Patients with Gram–Negative Sepsis, Abstract presented at 13th International Symposium on Intensive Care and Emergency Medicine, (Brussels, Belgium) (Mar. 1993).

Weiss and Olsson, "Cellular and Subcellular Localization of the Bactericidal/Permeability–Increasing Protein of Neutrophils", *Blood,* 69(2):652–659 (Feb. 1987).

Weiss et al., "Human Bactericidal/Permeability–Increasing Protein and a Recombinant $NH_2$–Terminal Fragment Cause Killing of Serum–resistant Gram–negative Bacteria in Whole Blood and Inhibit Tumor Necrosis Factor Release Induced by the Bacteria", *J. Clin. Invest.* 90:1122–1130 (Sep. 1992).

Weiss et al., "Purification and Characterization of a Potent Bactericidal and Membrane Active Protein from the Granules of Human Polymorphonuclear Leukocytes", *J. Biol. Chem.,* 253(8):2664–2672 (Apr. 25, 1978).

White et al., "Measurement of bactericidal/permeability–increasing protein in human body fluids by sandwich ELISA", *J. Immunol. Methods,* 167:227–235 (1994).

Wright et al., "CD14, a Receptor for Complexes of Lipopolysaccharide (LPS) and LPS Binding Protein", *Science,* 249:1431–1433 (Sep. 21, 1990).

METHOD FOR QUANTIFYING LBP IN BODY FLUIDS

This application is a continuation-in-part of U.S. patent application Ser. No. 08/186,811 filed Jan. 24, 1994, now U.S. Pat. No. 5,484,705.

BACKGROUND OF THE INVENTION

The present invention relates to methods for determination of the presence of Lipopolysaccharide binding protein (LBP) in body fluid samples including blood samples.

Lipopolysaccharide (LPS) is a common component of the outer membrane of Gram-negative bacteria and is responsible for many of the pathologic effects associated with gram-negative bacterial infection and endotoxemia. Because of the association between bacterial infection and sepsis, attempts have been made to correlate serum/plasma levels of endotoxin with disease. Typically, endotoxin levels have been measured using the Limulus amebocyte lysate (LAL) assay, in which endotoxin initiates a coagulation cascade that can be measured physically, turbidimetrically, or spectrophotometrically, Despite these attempts, however, no reliable correlations between endotoxin levels and sepsis severity or outcome have been identified. This is most likely due to the fact that (i) endotoxin levels in septic patients are very low (>10 pg/L), several serum proteins interfere with the proteolytic LAL cascade, (iii) endotoxin, once in contact with blood, can be "detoxified" by interaction with a variety of blood components, including high-density lipoprotein (HDL) and low-density lipoprotein (LDL) and (iv) endotoxin from different gram-negative organisms varies in its ability to trigger the LAL cascade. Thus, the absolute levels of endotoxin in a patient sample may not correspond to the actual concentrations of bioactive endotoxin present in in vivo.

Two related proteins have been identified in humans and other animals that bind LPS with high affinity. These two proteins, Lipopolysaccharide binding protein (LBP), and bactericidal/permeability increasing protein (BPI) have roughly the same molecular weight and share 45% amino acid homology, yet exhibit distinct physiological differences. LBP is a 60 kD glycoprotein synthesized in the liver, while BPI is found in the azurophilic granules of neutrophils. IBP is found in the serum of normal humans at levels of 5–10 $\mu$g/mL but can reach levels of 50–100 $\mu$g/mL in septic patients. Schumann et al., *Science*, 249:1429 (1990) disclose the amino acid sequences and encoding cDNA of both human and rabbit LBP. Like BPI, LBP has a binding site for lipid A and binds to the LPS from rough (R–) and smooth (S–) form bacteria. Unlike BPI, LBP does not possess significant bactericidal activity. BPI has been observed to neutralize and inhibit the production of TNF resulting from interaction of LBP with LPS and CD14 on monocytes and macrophages. Marra et al., *J. Immunol.* 148:532 (1992), Weiss et al., J. Clin. Invest. 90:1122 (1992). In contrast, LBP is observed to enhance LPS-induced TNF production. Wright et al., *Science,* 249:1131 (1990). Thus, in contrast to BPI, LBP has been recognized as an immunostimulatory molecule. See, e.g., Seilhamer, PCT International Application WO 93/06228 which discloses a variant form of LBP which it terms LBP-β. Also of interest to the present invention are Ulevitch, PCT International Application WO 91/01639 which discloses, among other things, anti-LBP antibodies as an anti-sepsis therapeutic agent and U.S. Pat. No. 5,245,013 which relates to LBP and discloses antibodies which immunoreact with a polypeptide having homology to LBP.

LBP has been characterized in the art as an "acute phase protein", that is one of many plasma proteins (such as C-reactive protein, fibrinogen and serum amyloid A) that increase in concentration in response to infectious and non-infectious tissue destructive processes. As such, it would be anticipated that LBP levels would be elevated in samples from patients suffering from a number of autoimmune diseases such as rheumatoid arthritis and lupus erythematosus.

Of interest to the present invention are disclosures related to the assaying of BPI activity in subjects. von der Mohien et al., Abstract, 13th International Symposium on Intensive Care and Emergency Medicine, Brussels (March 1993) discloses the results of assays for serum levels of BPI in patients with gram-negative sepsis and healthy subjects. The abstract disclosed that no BPI was detectable under the conditions of the assay in the serum of healthy subjects while circulating BPI was detected in all septic patients. Also of interest is the disclosure of co-owned and copending U.S. patent application Ser. No. 08/175,276 filed Dec. 29, 1993, now U.S. Pat. No. 5,466,581 which is a continuation-in-part of application Ser. No. 08/125,677 filed Sep. 22, 1993 the disclosures of which are hereby incorporated by reference. Those patent applications disclose that levels of BPI in blood plasma samples correlate with the presence or absence of sepsis while levels of BPI in blood serum samples do not. The patent applications teach that levels of BPI present in serum are not representative of endogenous extracellular levels of BPI in circulating blood while levels of BPI in plasma are.

Also of interest to the present invention are the disclosures of Leturcq et al., Keystone Tahoe Endotoxin Conference, Mar., 1–7, 1992 (Abstract) in which the generation of monoclonal antibodies to human LBP is reported. Also reported is the screening of normal human serum samples for the presence of LBP. LBP levels for normal serum samples were reported to range from 1 $\mu$g/mL to 24 $\mu$g/mL with an average of 7 $\mu$g/mL. Further of interest is the disclosure of Richard Ulevitch at the American Society for Microbiology General Meeting in Atlanta, Ga. May 16–21 (1993) at which data was presented on LBP and soluble CD14 levels in the serum of septic and healthy individuals. The average soluble CD14 and LBP concentrations in the serum of healthy adults were 1 $\mu$g/mL and 7 $\mu$g/mL respectively. The average soluble CD14 and LBP concentrations in the serum of septic patients were reported to be 2 $\mu$g/mL and 55 $\mu$g/mL respectively.

Geller et al., *Arch. Surg.,* 128:22–28 (1993) disclose experiments in which the induction of LBP mRNA was studied in three models known to induce acute phase responses: (1) LPS injection; (2) *Corynebacterium parvum* injection; and (3) turpentine injection. The publication reports that LBP mRNA is induced during hepatic inflammation and suggest that LBP is an acute-phase protein important in regulating the in vivo response to endotoxin.

Gallay et al., *Infect. Immun.,* 61:378–383 (1993) disclose that an acute phase response in mice injected with silver nitrate induced LBP synthesis, and that LBP levels increase approximately 10-fold over normal levels after an acute-phase response.

There exists a desire in the art for methods for determining the exposure of subjects to endotoxin and for distinguishing the effects of exposure to endotoxin from other acute phase physiologic responses. Also desired are methods for diagnosing the presence or severity of gram-negative sepsis in a subject and for predicting the prognosis of a subject suffering from sepsis.

SUMMARY OF THE INVENTION

The present invention provides methods for determining exposure of a subject to endotoxin by assaying for LBP. The invention further provides methods for screening for exposure to gram-negative bacterial endotoxin in an acute phase response in humans by assaying for LBP. Specifically, the method comprises the steps of determining the concentration of LBP in a sample of body fluid from the subject and correlating the concentration of LBP with a standard indicative of the exposure to endotoxin. Such standards can include a subjective standard for a given subject determined by LBP levels of that subject in a pretreatment state such as prior to undergoing surgery. Exposure to endotoxin as a consequence of such surgery can be determined by comparing post-surgical LBP levels with the standard established prior to surgery for that subject. Where access to a pretreatment standard level of LBP is not available for a given individual, objective standards based upon population or subpopulation averages may be applied for comparison. One such standard can be a concentration greater than approximately 15 μg/mL in human plasma or serum, as determined herein for LBP values in subjects suffering from numerous disease states. Subjects exhibiting LBP levels above that standard could presumptively be diagnosed as suffering from exposure to endotoxin while those having levels below that standard would not be. It is clear that alternative standards could be established depending upon the desired sensitivity and selectivity of an assay method and upon the subpopulation in which a given subject falls. For example, standards might be established at different levels for different ages, genders, ethnicities and underlying health conditions of various subpopulations. Moreover, it should be understood that standard levels will differ according to the identity of the particular body fluid which is assayed.

The invention further provides methods for diagnosing the presence or severity of sepsis in a subject comprising the steps of determining the concentration of LBP in a sample of body fluid from the subject and correlating the concentration of LBP with a standard indicative of the presence or severity of sepsis. The invention further provides methods for predicting the prognosis of a subject suffering from sepsis comprising the steps of determining the concentration of LBP in a sample of body fluid from the subject and correlating the concentration of LBP with a standard indicative of the prognosis of a subject suffering from sepsis.

DETAILED DESCRIPTION OF THE INVENTION

Figure 1:
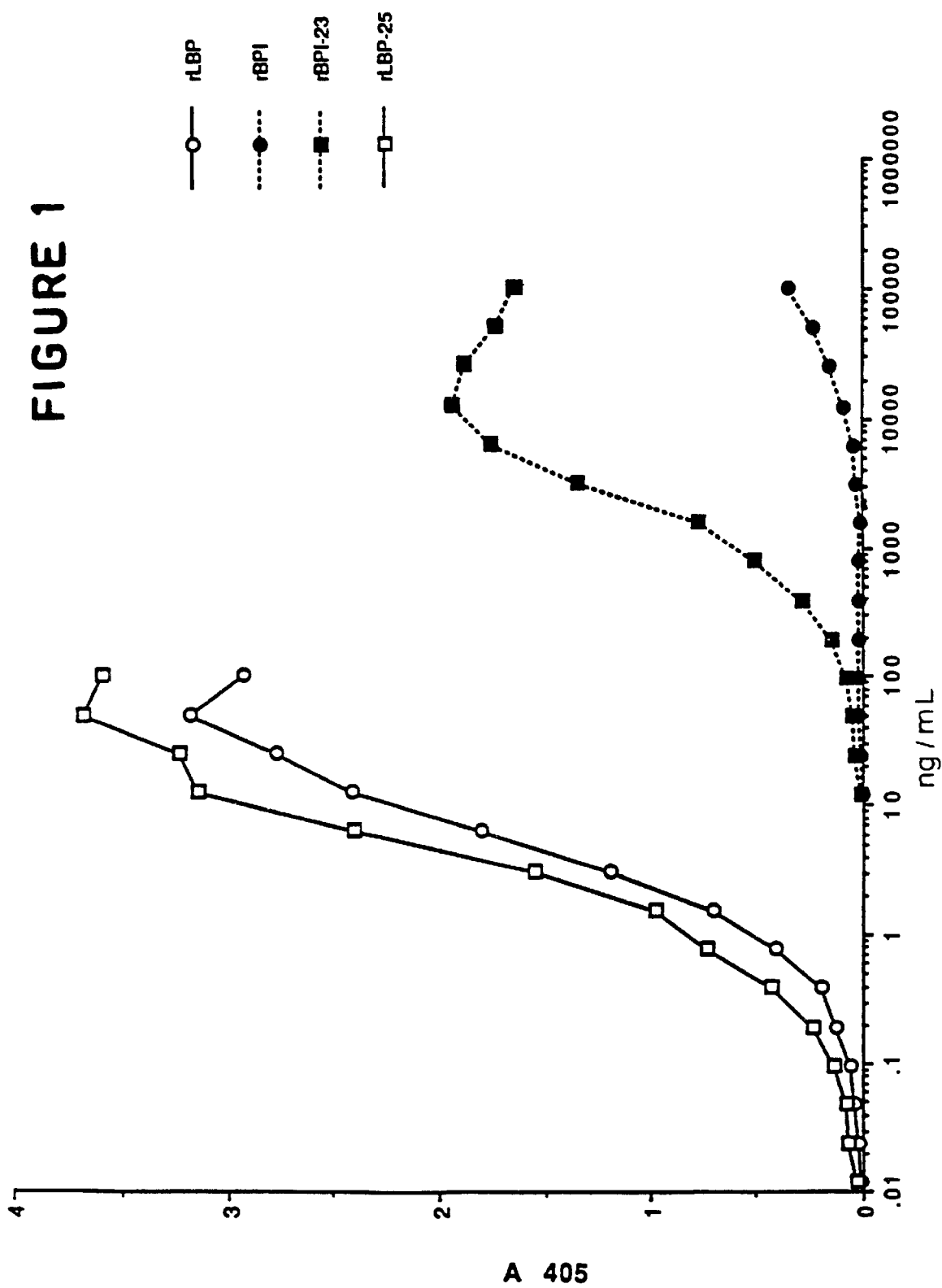
FIG. 1 depicts the dose-response curves for rLBP, rLBP$_{25}$, rBPI and rBPI$_{23}$ in LBP sandwich assays.

The present invention relates to methods for quantifying the presence of LBP in body fluids including blood. While the assay can be used to determine the presence and quantity of LBP which has been administered therapeutically, it is particularly useful for quantifying the presence of endogenous LBP in circulating blood as an indication of exposure of a subject to endotoxin. Moreover, quantifying the presence of LBP is contemplated to be useful in diagnostic and prognostic methods for evaluating gram- negative sepsis patients.

The present invention provides a sandwich ELISA assay for human LBP which exhibits high assay sensitivity, high specificity, and excellent reproducibility. As used herein "LBP" quantitated according to assay methods includes native LBP, recombinant LBP, LBP fragments and analogs as well as other LBP proteins and protein products.

The amino acid and nucleotide sequence of recombinant LBP are set out in co-owned and copending U.S. patent application Ser. No. 08/029,510 filed Jun. 17, 1993 as shown in SEQ ID NOS: 1 and 2 herein. A recombinant LBP amino-terminal fragment is characterized by the amino acid sequence of the first 197 amino acids of the amino-terminus of LBP as set out in SEQ ID NOS: 3 and 4 the production of which is described in co-owned and copending U.S. patent application Ser. No. 08/079,510 filed Jun. 12, 1993 the disclosure of which is incorporated herein. Such LBP protein products may be readily quantified using assays including immunological assays and bioassays in the subnanogram per mL range. Immunological assays capable of quantifying LBP are preferably carried out by enzyme linked immunosorbant (ELISA) sandwich assays but competitive assays and immunological assays utilizing other labelling formats may also be used. Preferred assays of the invention utilize anti-LBP antibodies, including monoclonal antibodies and affinity-purified rabbit polyclonal antibodies. Rabbit polyclonal anti-LBP antibodies may be prepared according to conventional methods using LBP as an immunogen. Non-immunological methods may also be used to assay for LBP. As one example, Ulevitch et al., U.S. Pat. No. 5,245,013 disclose assay methods comprising binding of LBP to LPS and separating the complex by a centrifugation density gradient method. As another example, Geller et al., *Arch. Surg.* 128:22–28 (1993) disclose IBP bioactivity assays in which IL-6 and TNF upregulation are measured.

Body fluids which can be assayed for the presence of LBP include whole blood with blood serum and blood plasma being preferred. Because LBP is a serum protein it is contemplated that it could be excreted and that analysis of LBP levels in urine may provide diagnostic and prognostic utility. The LBP immunoassays of the invention may also be used to determine the concentration of LBP in other body fluids including, but not limited to lung lavages, viterous fluid, crevicular fluid, cerebralspinal fluid, saliva and synovial fluid.

Because LBP has been characterized as an "acute phase protein" it would be expected that LBP levels would be elevated in subjects suffering from autoimmune diseases. As one aspect of the present invention it has been found that LBP levels are not generally elevated over normal in subjects suffering from acute lymphoblastic leukemia (ALL), acute graft versus host disease (aGvHD), chronic lymphocytic leukemia (CLL), cutaneous T-cell lymphoma (CTCL), type 1 diabetes, aplastic anemia (AA), Crohn's Disease, psoriasis, rheumatoid arthritis (RA), scleroderma, and systemic lupus erythematosus (SLE).

Certain subjects tentatively identified as suffering from gram-negative sepsis but ultimately identified as suffering from gram-positive sepsis also had elevated LBP levels. It is noted that translocation of bacteria and/or endotoxin from the gut into the bloodstream can occur in any infection. Thus, infections due to gram-positive bacteria or fungi may also lead to the presence of endotoxin or gram-negative bacteria in the blood and, therefore elevated levels of LBP.

The present invention is based in part upon the observation that serum and plasma levels of LBP directly correlate with a subject's exposure to biologically active LPS. Moreover, LBP levels appear to correlate with survival in suspected gram-negative sepsis patients. For example, subjects with levels of circulating LBP below 27.3 µg/mL (the median value for 58 subjects suffering from gram-negative sepsis) tended to have a greater 14 day survival than did those subjects with levels of LBP above that median. Further, for example, when a plasma LBP threshold level was set at 46 µg/mL, those subjects having a pretreatment LBP plasma level less than 46 µg/mL had a significantly greater survival rate (p=0.004) over a 27 day period than did those subjects having a pretreatment plasma LBP level greater than 46 µg/mL.

It is further contemplated by the invention that elevated levels of LBP may result from exposure to larger amounts of endotoxin, and may therefore be diagnostic of greater infection and/or endotoxemia severity. Elevated levels of LBP may also be used to indicate the suitability of using antibiotics directed against gram-negative bacteria or other therapeutic agents targeted directly to endotoxin such as BPI or anti-endotoxin antibodies including the monoclonal antibody E5.

Other aspects and advantages of the present invention will be understood upon consideration of the following illustrative examples. Example 1 relates to the preparation of affinity purified rabbit anti-BPI antibodies; Example 2 relates to the biotin labeling of such antibodies; and Example 3 relates to ELISA procedures utilizing such antibodies. Example 4 relates to the comparative immunoreactivity of rLBP, rLBP$_{25}$, rBPI AND rBPI$_{23}$. Example 5 relates to the measurement of rLBP spiked into pooled human plasma; and Example 6 relates to the comparison of LBP levels in human plasma and serum. Example 7 relates to the clinical correlations of endogenous IBP immunoreactivity with sepsis and other disease states in human plasma; and Example 8 relates to the effect of LPS administration on endogenous IBP levels in healthy subjects. Example 9 relates to clinical correlations between plasma LBP levels and survival in suspected gram-negative sepsis patients; and Example 10 relates to clinical correlations of acute phase proteins in healthy, rheumatoid arthritic and septic patients.

EXAMPLE 1

PREPARATION OF AFFINITY PURIFIED RABBIT ANTI-rLBP ANTIBODY

According to this example affinity purified rabbit anti-rLBP antibody was prepared. Specifically, rLBP (20 mg) produced according to co-owned and copending U.S. patent application Ser. No. 08/079,510 filed Jun. 17, 1993, the disclosure of which is hereby incorporated by reference was coupled to 10 mL of cyanogen bromide-activated Sepharose 4B (Sigma Chemical Co., St Louis, MO) in 0.2 M bicarbonate, pH 8.6, containing 0.5 NaCl. Approximately 94% of the rLBP was coupled to the resin. Pooled antisera (125 mL) from two rabbits, immunized initially with rLBP$_{25}$ produced according to the methods of U.S. patent application Ser. No. 08/079,510 filed Jun. 17, 1993 and thereafter with rLBP, were diluted with an equal volume of phosphate buffered saline, pH 7.2 (PBS). A portion (50 mL) of the diluted antisera was passed through the 10 mL rLBP-Sepharose column; the column was then washed with PBS and bound antibodies were eluted with 0.1 M glycine, pH 2.5. Collected fractions were immediately neutralized with 1 M phosphate buffer, pH 8.0. Peak fractions were identified by measuring absorbance at 280 nm according to the method of Harlow et al., Antibodies: A Laboratory Manual, Cold Springs Harbor Laboratory Press, New York, p. 312 (1988). After several sequential column cycles, the affinity purified rabbit anti-LBP antibody was dialyzed against PBS-azide pH 7.2.

EXAMPLE 2

PREPARATION OF BIOTIN LABELED RABBIT ANTI-rLBP ANTIBODY

In this example twenty milligrams of affinity purified rabbit anti-rLBP antibody produced according to the method of Example 1 was incubated with 2 mg of biotinamidocaproate N-hydroxysuccinimide ester (Sigma Chemical Co., St. Louis, MO) in 11 mL of 0.1 M sodium bicarbonate pH 8.3 for two hours at room temperature. Unconjugated biotin was removed and the alkaline buffer exchanged by fractionating the reaction mixture on a PD-10 column (Pharmacia Biotech Inc., Piscataway, NJ) equilibrated with PBS containing 0.1% sodium azide.

EXAMPLE 3

ELISA PROCEDURE

Fifty microliters of affinity purified rabbit anti-rLBP antibody (2 µg/mL in PBS) were incubated overnight at 2°–8° C. (or alternatively, 1 hour at 37° C.) in the wells of Immulon 2 (Dynatech Laboratories Inc., Chantilly, VA) microtiter plates. The antibody solution was removed and 200 µL of 1% non-fat milk in PBS (blocking agent) was added to all wells. After blocking the plates for 1 hour at room temperature, the wells were washed 3 times with 300 µL of wash buffer (PBS/0.05% Tween-20).

Standards, samples and controls were diluted in triplicate with PBS containing 1% bovine serum albumin, 0.05% Tween 20 (PBS-BSA/Tween) and 10 units/mL of sodium heparin (Sigma Chemical Co., St. Louis, MO) in separate 96-well plates. rLBP or rLBP25 standard solutions were prepared as serial two-fold dilutions from 100 to 0.012 ng/mL. Each replicate and dilution of the standards, samples and controls (50 µL) was transferred to the blocked microtiter plates and incubated for 1 hour at 37° C. After the primary incubation, the wells were washed 3 times with wash buffer. Biotin-labeled rabbit anti-LBP antibody was diluted ½000 in PBS-BSA/Tween and 50 µL was added to all wells. The plates were then incubated for 1 hour at 37° C. Subsequently, all wells were washed 3 times with wash buffer. Alkaline phosphatase-labeled streptavidin (Zymed Laboratories Inc., San Francisco, CA) was diluted ½000 in PBS-BSA/Tween and 50 µL was added to all wells. After incubation for 15 minutes at 37° C., all wells were washed 3 times with wash buffer and 3 times with deionized water and the chromogenic substrate p-nitrophenylphosphate (1 mg/mL in 10% diethanolamine buffer) was added in a volume of 50 µL to all wells. Color development was allowed to proceed for 1 hour at room temperature, after which 50 µL of 1 N NaOH was added to stop the reaction. The absorbance at 405 nm was determined for all wells using a Vmax Plate Reader (Molecular Devices Corp., Menlo Park, CA).

The mean absorbance at 405 nm ($A_{405}$) for all samples and standards (in triplicate) were corrected for background by subtracting the mean $A_{405}$ of wells receiving only sample dilution buffer (no LBP) in the primary incubation step. A standard curve was then plotted as $A_{405}$ versus ng/mL of rLBP or $rLBP_{25}$. The linear range was selected, a linear regression analysis was performed and concentrations were determined for samples and controls by interpolation from the standard curve.

EXAMPLE 4

COMPARATIVE IMMUNOREACTIVITY OF rLBP, $LBP_{25}$, rBPI AND $rBPI_{23}$

In this example, the immunoreactivity of rLBP, $rLBP_{25}$, rBPI and $rBPI_{23}$ were compared in the BPI sandwich ELISA to determine possible immunologic cross-reactivity. Despite considerable sequence homology between LBP and BPI (see, e.g., Schumann et al., *Science*, 249:1429 (1990), the results illustrated in FIG. 1 show that, on a mass basis, $rBPI_{23}$ produced a signal which was approximately 3 orders of magnitude lower than that of rLBP2 and rLBP, while rBPI produced a signal that was approximately 5 orders of magnitude lower than that of rLBP and $rLBP_{25}$. For example, a concentration of 100,000 ng/mL (100 µg/mL) of rBPI or 400 ng/mL $rBPI_{23}$ generated a signal which was equal to that produced by 0.8 ng/mL of rLBP or 0.4 ng/mL of $rLBP_{25}$. These results demonstrate minimal cross-reactivity of the antibody with BPI and confirm the specificity of the assay for LBP.

EXAMPLE 5

MEASUREMENT OF rLBP SPIKED INTO POOLED HUMAN PLASMA

In this example, the recovery of rLBP in human blood fluids was evaluated by examining pooled human plasma spiked with different concentrations of rLBP and then frozen and thawed prior to measurement in the sandwich ELISA. Recovery of spiked LBP was defined as the amount of LBP measured in spiked human plasma samples minus the concentration in the unspiked control, divided by the actual amount spiked in the sample. The fraction recovered was multiplied by 100 and the results were expressed as a percentage of the input concentration. Recovery of different concentrations of rLBP spiked into pooled human plasma samples averaged 68% and ranged 5 from 59% at 42 µg/mL to 78% at 168 µg/mL. Table I summarizes the recovery data for each LBP spiked plasma sample.

TABLE I

Recovery of rLBP Spiked into Pooled Citrated Human Plasma

| Amount Spiked (µg/mL) | Amount Measured (µg/mL) | Amount Recovered (µg/mL) | Percent Recovery |
|---|---|---|---|
| 0 | 2.47 | — | — |
| 10.5 | 9.85 | 7.38 | 70% |
| 21 | 16.1 | 13.63 | 65% |
| 42 | 27.3 | 24.83 | 59% |
| 84 | 60.8 | 58.33 | 69% |
| 168 | 133 | 130.53 | 78% |
|  |  | Mean Recovery | 68% |

EXAMPLE 6

COMPARISON OF PLASMA AND SERUM LBP LEVELS

According to this example concentrations of LBP in the serum and plasma of healthy subjects were assayed and compared utilizing the sandwich ELISA assay according to Example 3. Plasma concentrations of LBP were found to be essentially the same as serum concentrations for LBP when the plasma volume was corrected for dilution (dividing by a factor of 0.85) resulting from the addition of anticoagulant. Plasma concentrations in normal human subjects were found to be 3.1 µg/mL (S.D. 0.9 µg/mL) or 3.7 µg/mL (S.D. 1.1 µl/mL) corrected, compared with 3.7 µg/mL (S.D. 0.9 µg/mL) for serum.

EXAMPLE 7

CLINICAL CORRELATIONS OF ENDOGENOUS LBP IMMUNOREACTIVITY IN HUMAN PLASMA

Figure 2:
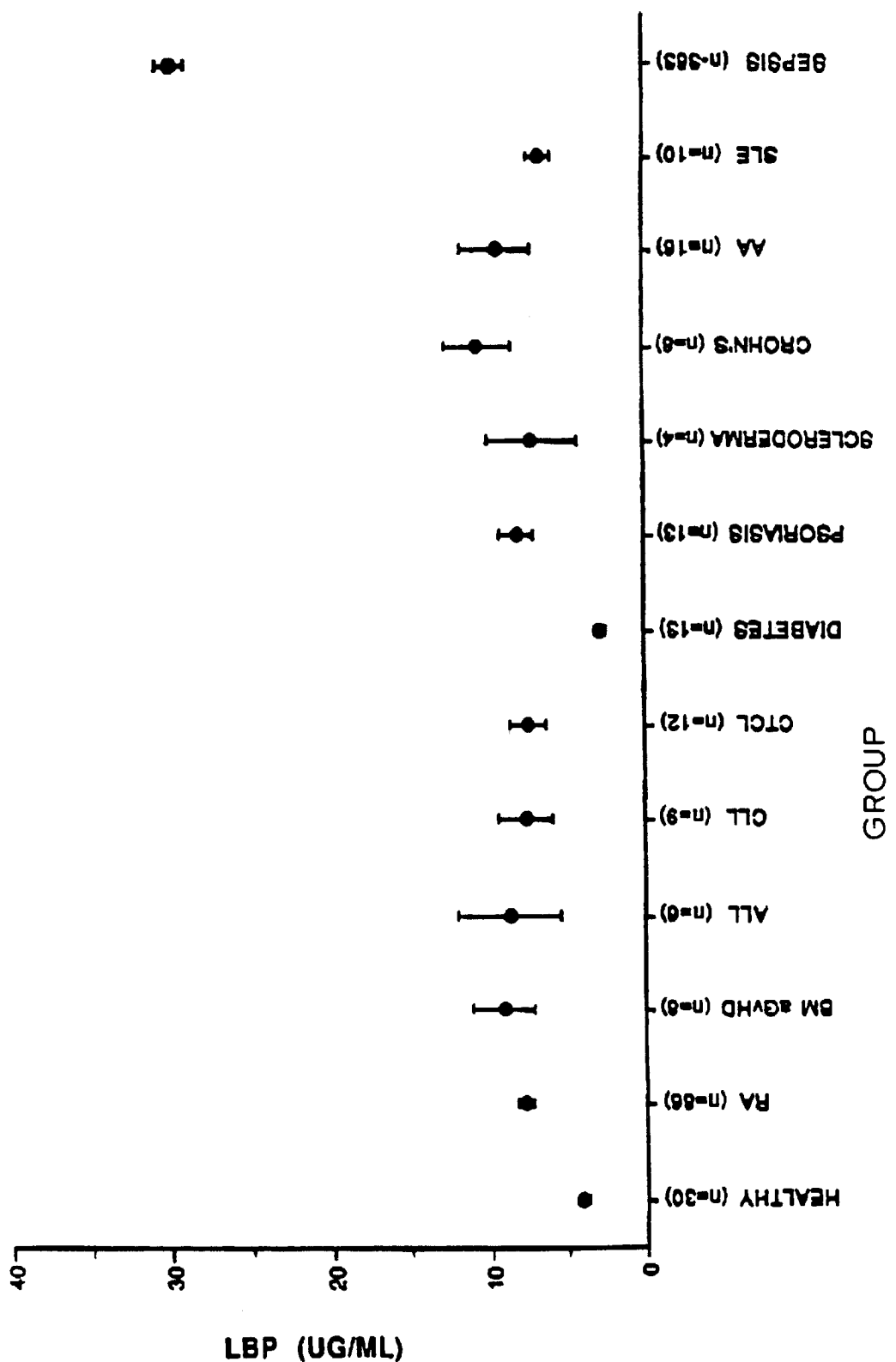
FIG. 2 depicts LBP levels (mean±standard error) in the plasma of healthy human subjects and human subjects suffering from various disease states.

In this example endogenous LBP immunoreactivity was measured in human plasma or serum samples collected from a variety of subjects suffering from gram-negative sepsis and a variety of other clinical conditions. Specifically, plasma samples of healthy individuals (30 subjects) and individuals diagnosed with gram-negative sepsis (363 subjects) were assayed for LBP levels. Serum samples of individuals with acute lymphoblastic leukemia (ALL) (6 subjects); acute graft versus host disease (aGvHD) (8 subjects); chronic lymphocytic leukemia (CLL) (9 subjects); cutaneous T-cell lymphoma (CTCL) (12 subjects); type 1 diabetes (13 subjects); aplastic anemia (AA) (16 subjects); Crohn's Disease (8 subjects); psoriasis (13 subjects); rheumatoid arthritis (RA) (86 subjects); scleroderma (4 subjects), and systemic lupus erythematosus (SLE) (10 subjects) were assayed for LBP levels. The results are shown in FIG. 2.

While LBP levels among subjects diagnosed as suffering from gram-negative sepsis were elevated it was found that LBP levels are not elevated over normal in subjects suffering from acute lymphoblastic leukemia, acute graft versus host disease, chronic lymphocytic leukemia, cutaneous T-cell lymphoma, type 1 diabetes, aplastic anemia, Crohn's Disease, psoriasis, rheumatoid arthritis, scleroderma, and systemic lupus erythematosus (SLE). Accordingly, the LBP assay of the invention is valuable for distinguishing conditions associated with endotoxin from other acute phase conditions (such as RA, SLE and the like).

EXAMPLE 8

THE EFFECT OF LPS ADMINISTRATION ON ENDOGENOUS LBP LEVELS IN HEALTHY SUBJECTS

Figure 3:
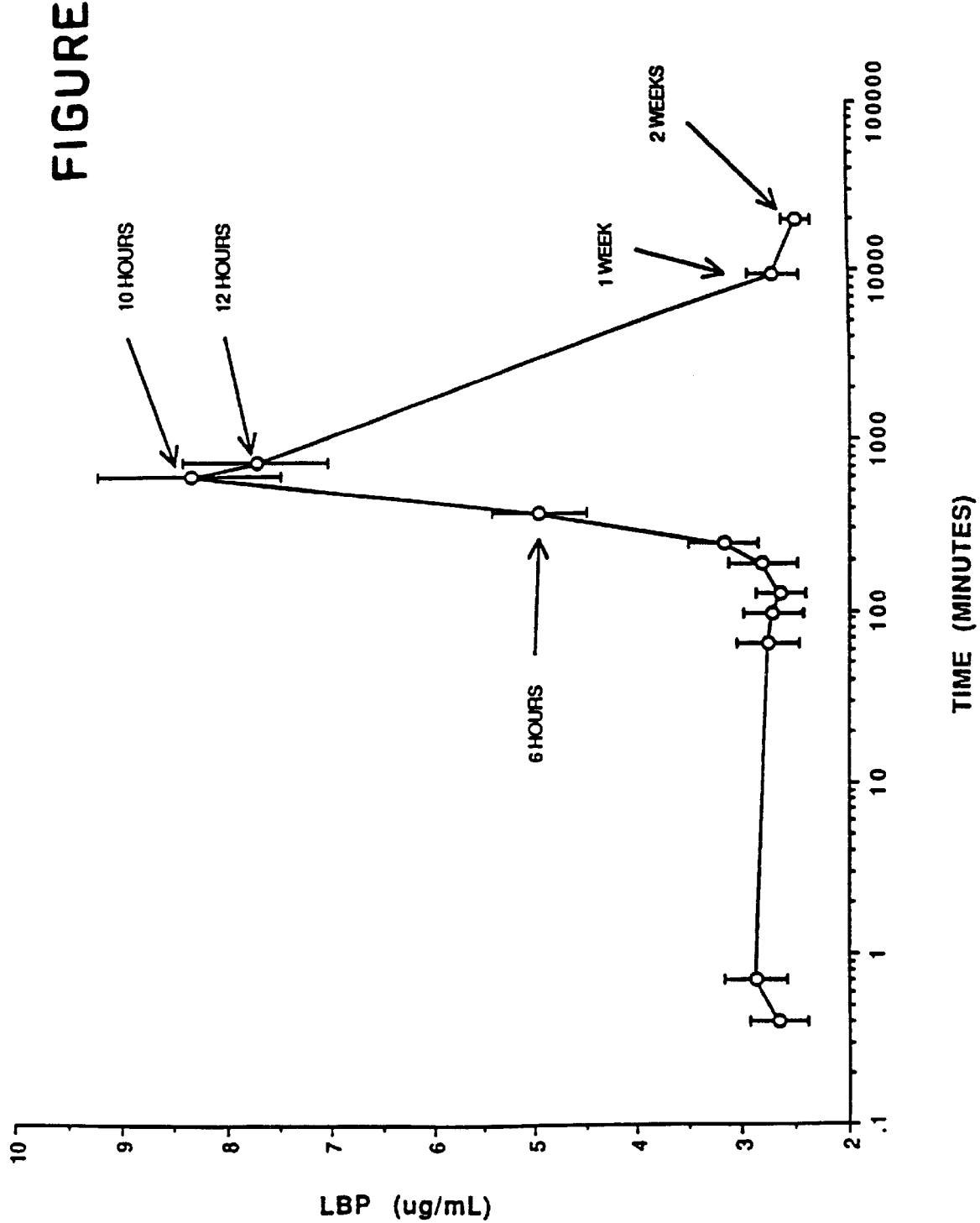
FIG. 3 depicts LBP levels (mean±standard error) in healthy subjects treated with LPS.

In this example, the effect of LPS administration on endogenous LBP immunoreactivity in healthy human subjects was determined. Specifically, healthy subjects were monitored utilizing the LBP sandwich assay for changes in LBP plasma levels at various time points after intravenous administration of 4 ng/kg LPS (16 subjects) or in control subjects (2) not receiving LPS. The results illustrated in FIG. 3 show the change in mean plasma LBP concentration with time. For those subjects treated with LPS LBP levels began to rise about 6 hours after LPS administration. Peak LBP plasma levels were observed in most subjects between 10 to 12 hours after the LPS administration. The average increase from baseline to peak LBP level was approximately 3-fold. Over this time period the mean LBP levels in control subjects remained within normal range (approximately 5 µg/mL).

It is contemplated that additional analysis will illustrate the correlation of LBP levels in body fluids with the symptoms of exposure to endotoxin and that LBP levels will be diagnostic and prognostic of disease states resulting from exposure to endotoxin.

It is contemplated that additional analysis will illustrate the correlation of LBP levels with symptoms of bacterial infections, endotoxemia and sepsis including conditions associated with sepsis including DIC and ARDS.

EXAMPLE 9

CLINICAL CORRELATIONS BETWEEN PLASMA IBP LEVELS AND SURVIVAL IN SUSPECTED GRAM-NEGATIVE SEPSIS PATIENTS

Figure 4:
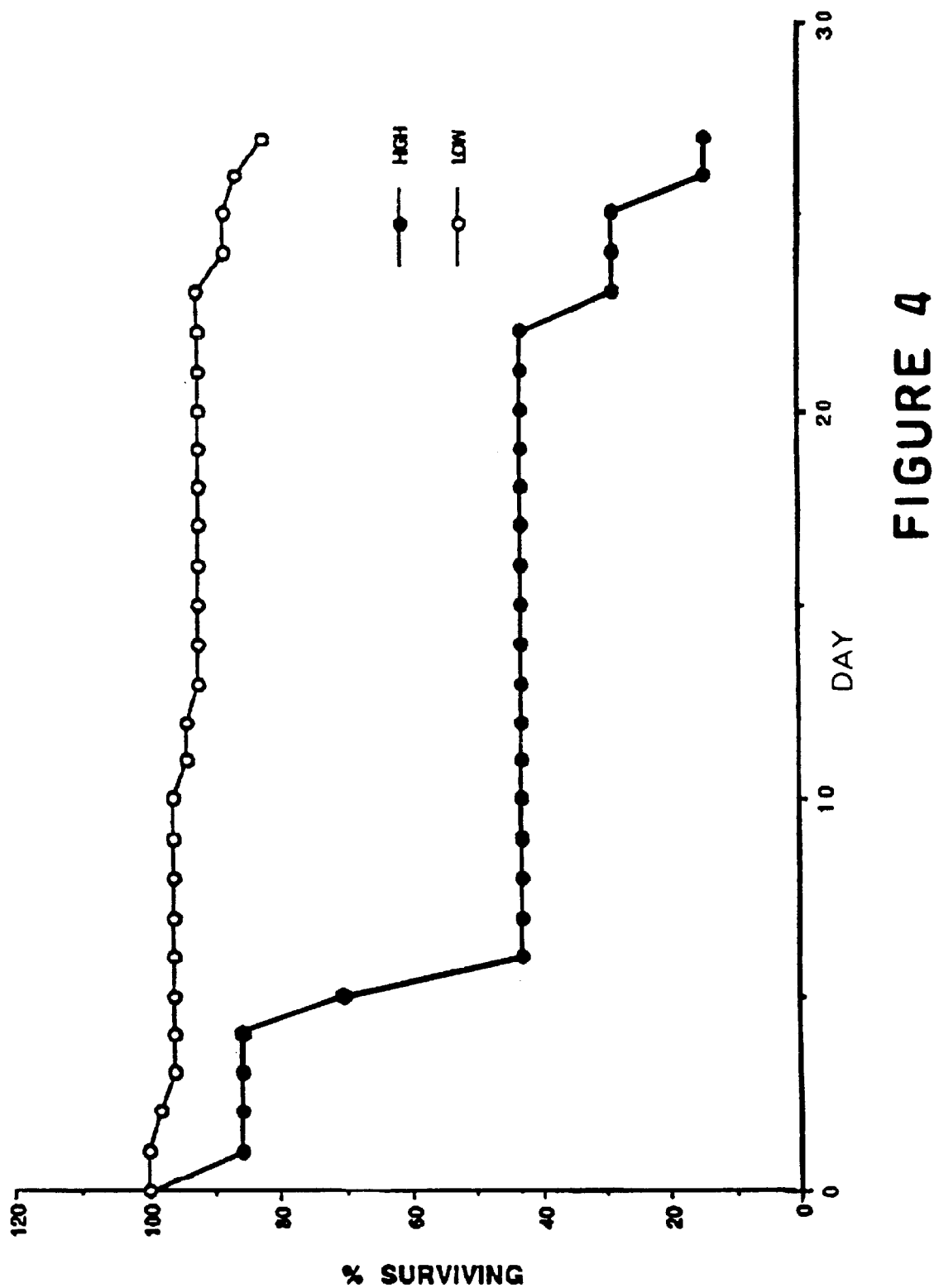
FIG. 4 depicts comparative survival in suspected gram-negative sepsis patients classified as having either high or low levels of plasma LBP.

Correlations between plasma LBP levels and survival in suspected gram-negative sepsis patients were compared using data obtained from the septic subjects described in Example 7. In this case, a standard LBP concentration was set at 46 μg/mL and patients with suspected gram-negative sepsis were classified as having either high (>46 μg/mL) or low (<46 μg/mL) LBP plasma levels as measured in pre-treatment samples. As shown in the data presented in FIG. 4, those subjects having low pretreatment plasma levels of LBP had a significantly greater survival rate (p=0.004) over a 27 day period than did those subjects having a high pretreatment plasma LBP level. These data show the utility of assaying LBP levels and comparing them to a standard LBP value for predicting the prognosis of subjects suffering from sepsis.

EXAMPLE 10

CLINICAL CORRELATIONS OF ACUTE PHASE PROTEINS IN HEALTHY, RHEUMATOID ARTHRITIC, AND SEPTIC PATIENTS

Figure 5A:
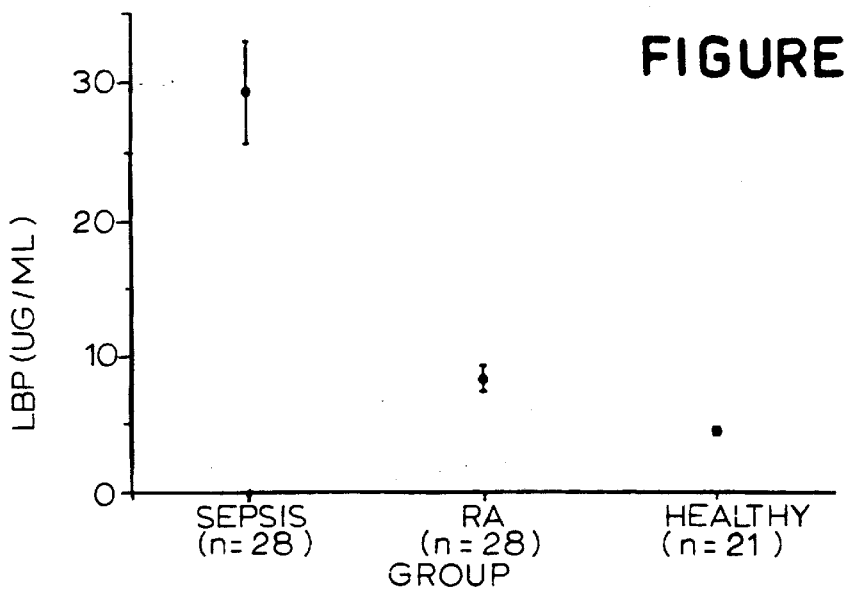
FIGS. 5a, 5b and 5c depict LBP, C-reactive protein (CRP) and fibrinogen levels (mean±standard error), respectively in healthy, rheumatoid arthritic and septic subjects.
Figure 5B:
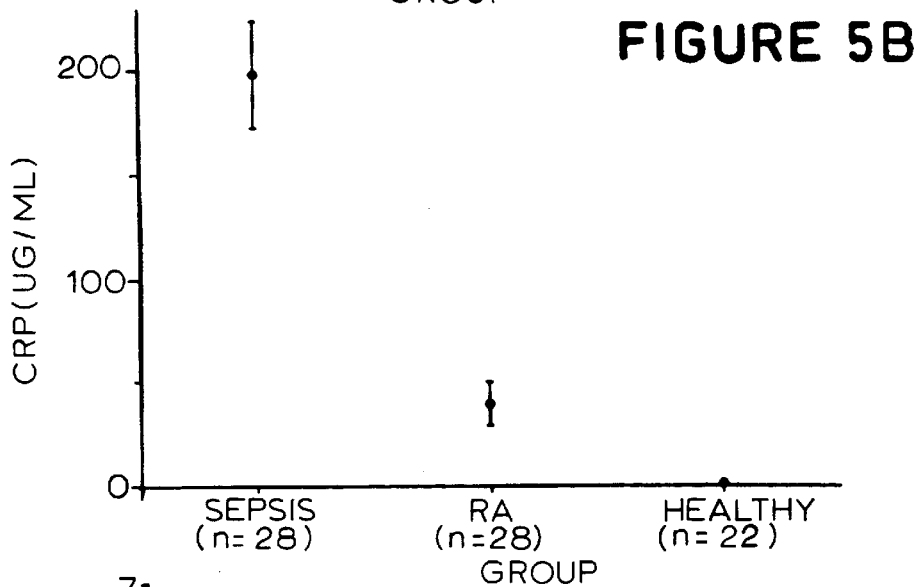
Figure 5C:
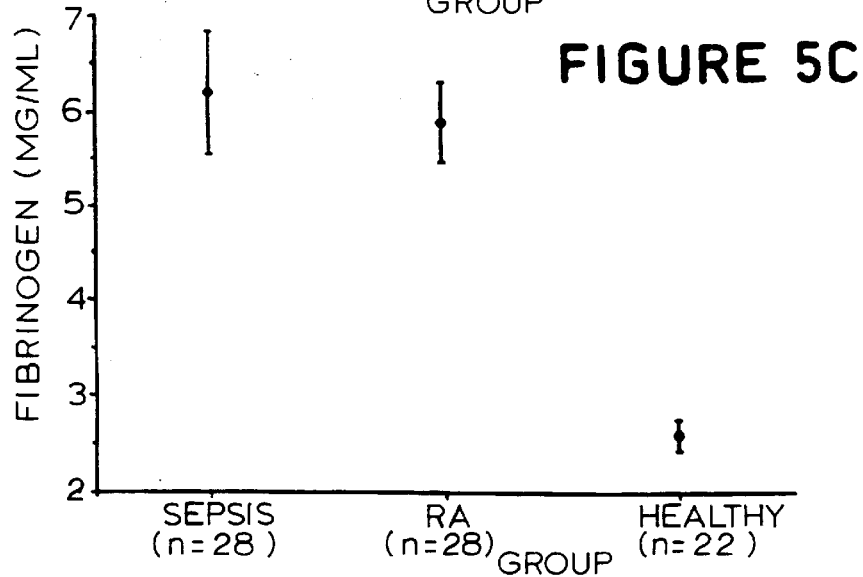

Plasma levels of LBP, C-reactive protein (CRP) and fibrinogen were measured in small groups of healthy, rheumatoid arthritic and septic patients with the results shown in FIGS. 5a (LBP levels), 5b (CRP levels) and 5c (fibrinogen levels). The results show that relative to healthy subjects, mean fibrinogen levels were elevated approximately 2.5 fold for both rheumatoid arthritic and septic subjects. Relative to healthy subjects, mean CRP levels were found to be elevated approximately 40-fold for rheumatoid arthritic subjects and 200-fold for septic subjects. In contrast, and consistent with the results in Example 7, mean LBP levels were only slightly increased (less than 2-fold) for rheumatoid arthritis subjects while the mean LBP levels were increased by more than 6 fold for septic subjects.

Numerous modifications and variations in the practice of the invention are expected to occur to those skilled in the art upon consideration of the foregoing description of the presently preferred embodiments thereof. Consequently, the only limitations which should be placed upon the scope of the present invention are those which appear in the appended claims.

What is claimed is:

1. A method for determining exposure of a human subject to endotoxin in the absence of an acute phase response comprising the steps of determining the concentration of lipopolysaccharide binding protein in a sample of body fluid from the subject and correlating the concentration of lipopolysaccharide binding protein with a standard indicative of exposure to endotoxin.

2. The method of claim 1 wherein said sample is a blood sample.

3. The method of claim 1 wherein said sample is a plasma or serum sample.

4. The method of claim 1 wherein the concentration of lipopolysaccharide binding protein is determined by means of an immunoassay.

5. The method of claim 4 wherein the immunoassay is a sandwich immunoassay.

6. A method for determining the prognosis of a human subject suffering from a disease state resulting from exposure to endotoxin comprising the steps of determining the concentration of lipopolysaccharide binding protein in a sample of body fluid from the subject and correlating the concentration of lipopolysaccharide binding protein with a standard indicative of exposure to endotoxin, wherein an increased or increasing level of lipopolysaccharide binding protein is indicative of adverse prognosis.

7. The method of claim 6 wherein said sample is a blood sample.

8. The method of claim 6 wherein said sample is a plasma or serum sample.

9. The method of claim 6 wherein the concentration of lipopolysaccharide binding protein is determined by means of an immunoassay.

10. The method of claim 9 wherein the immunoassay is a sandwich immunoassay.

11. The method of claim 6 wherein the standard is a concentration which is greater than a lipopolysaccharide binding protein concentration for said subject determined during a period prior to exposure to endotoxin.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1443 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: 1..1443

( i x ) FEATURE:
        ( A ) NAME/KEY: mat_peptide
        ( B ) LOCATION: 76..1443

( i x ) FEATURE:
        ( A ) NAME/KEY: misc_feature
        ( D ) OTHER INFORMATION: "rLBP"

( x i ) SEQUENCE DESCRIPTION: SEQ ID NO:1:

| ATG | GGG | GCC | TTG | GCC | AGA | GCC | CTG | CCG | TCC | ATA | CTG | CTG | GCA | TTG | CTG | 48 |
|---|---|---|---|---|---|---|---|---|---|---|---|---|---|---|---|---|
| Met | Gly | Ala | Leu | Ala | Arg | Ala | Leu | Pro | Ser | Ile | Leu | Leu | Ala | Leu | Leu | |
| -25 | | | | | -20 | | | | | -15 | | | | | -10 | |

| CTT | ACG | TCC | ACC | CCA | GAG | GCT | CTG | GGT | GCC | AAC | CCC | GGC | TTG | GTC | GCC | 96 |
|---|---|---|---|---|---|---|---|---|---|---|---|---|---|---|---|---|
| Leu | Thr | Ser | Thr | Pro | Glu | Ala | Leu | Gly | Ala | Asn | Pro | Gly | Leu | Val | Ala | |
| | | | | -5 | | | | | 1 | | | | 5 | | | |

| AGG | ATC | ACC | GAC | AAG | GGA | CTG | CAG | TAT | GCG | GCC | CAG | GAG | GGG | CTA | TTG | 144 |
|---|---|---|---|---|---|---|---|---|---|---|---|---|---|---|---|---|
| Arg | Ile | Thr | Asp | Lys | Gly | Leu | Gln | Tyr | Ala | Ala | Gln | Glu | Gly | Leu | Leu | |

```
                    10                          15                          20
GCT  CTG  CAG  AGT  GAG  CTG  CTC  AGG  ATC  ACG  CTG  CCT  GAC  TTC  ACC  GGG        192
Ala  Leu  Gln  Ser  Glu  Leu  Leu  Arg  Ile  Thr  Leu  Pro  Asp  Phe  Thr  Gly
     25                      30                      35

GAC  TTG  AGG  ATC  CCC  CAC  GTC  GGC  CGT  GGG  CGC  TAT  GAG  TTC  CAC  AGC        240
Asp  Leu  Arg  Ile  Pro  His  Val  Gly  Arg  Gly  Arg  Tyr  Glu  Phe  His  Ser
40                        45                       50                          55

CTG  AAC  ATC  CAC  AGC  TGT  GAG  CTG  CTT  CAC  TCT  GCG  CTG  AGG  CCT  GTC        288
Leu  Asn  Ile  His  Ser  Cys  Glu  Leu  Leu  His  Ser  Ala  Leu  Arg  Pro  Val
                    60                      65                           70

CCT  GGC  CAG  GGC  CTG  AGT  CTC  AGC  ATC  TCC  GAC  TCC  TCC  ATC  CGG  GTC        336
Pro  Gly  Gln  Gly  Leu  Ser  Leu  Ser  Ile  Ser  Asp  Ser  Ser  Ile  Arg  Val
               75                      80                      85

CAG  GGC  AGG  TGG  AAG  GTG  CGC  AAG  TCA  TTC  TTC  AAA  CTA  CAG  GGC  TCC        384
Gln  Gly  Arg  Trp  Lys  Val  Arg  Lys  Ser  Phe  Phe  Lys  Leu  Gln  Gly  Ser
          90                      95                      100

TTT  GAT  GTC  AGT  GTC  AAG  GGC  ATC  AGC  ATT  TCG  GTC  AAC  CTC  CTG  TTG        432
Phe  Asp  Val  Ser  Val  Lys  Gly  Ile  Ser  Ile  Ser  Val  Asn  Leu  Leu  Leu
     105                     110                     115

GGC  AGC  GAG  TCC  TCC  GGG  AGG  CCC  ACA  GTT  ACT  GCC  TCC  AGC  TGC  AGC        480
Gly  Ser  Glu  Ser  Ser  Gly  Arg  Pro  Thr  Val  Thr  Ala  Ser  Ser  Cys  Ser
120                     125                     130                          135

AGT  GAC  ATC  GCT  GAC  GTG  GAG  GTG  GAC  ATG  TCG  GGA  GAC  TTG  GGG  TGG        528
Ser  Asp  Ile  Ala  Asp  Val  Glu  Val  Asp  Met  Ser  Gly  Asp  Leu  Gly  Trp
                    140                     145                     150

CTG  TTG  AAC  CTC  TTC  CAC  AAC  CAG  ATT  GAG  TCC  AAG  TTC  CAG  AAA  GTA        576
Leu  Leu  Asn  Leu  Phe  His  Asn  Gln  Ile  Glu  Ser  Lys  Phe  Gln  Lys  Val
               155                     160                     165

CTG  GAG  AGC  AGG  ATT  TGC  GAA  ATG  ATC  CAG  AAA  TCG  GTG  TCC  TCC  GAT        624
Leu  Glu  Ser  Arg  Ile  Cys  Glu  Met  Ile  Gln  Lys  Ser  Val  Ser  Ser  Asp
          170                     175                     180

CTA  CAG  CCT  TAT  CTC  CAA  ACT  CTG  CCA  GTT  ACA  ACA  GAG  ATT  GAC  AGT        672
Leu  Gln  Pro  Tyr  Leu  Gln  Thr  Leu  Pro  Val  Thr  Thr  Glu  Ile  Asp  Ser
     185                     190                     195

TTC  GCC  GAC  ATT  GAT  TAT  AGC  TTA  GTG  GAA  GCC  CCT  CGG  GCA  ACA  GCC        720
Phe  Ala  Asp  Ile  Asp  Tyr  Ser  Leu  Val  Glu  Ala  Pro  Arg  Ala  Thr  Ala
200                     205                     210                          215

CAG  ATG  CTG  GAG  GTG  ATG  TTT  AAG  GGT  GAA  ATC  TTT  CAT  CGT  AAC  CAC        768
Gln  Met  Leu  Glu  Val  Met  Phe  Lys  Gly  Glu  Ile  Phe  His  Arg  Asn  His
                    220                     225                     230

CGT  TCT  CCA  GTT  ACC  CTC  CTT  GCT  GCA  GTC  ATG  AGC  CTT  CCT  GAG  GAA        816
Arg  Ser  Pro  Val  Thr  Leu  Leu  Ala  Ala  Val  Met  Ser  Leu  Pro  Glu  Glu
               235                     240                     245

CAC  AAC  AAA  ATG  GTC  TAC  TTT  GCC  ATC  TCG  GAT  TAT  GTC  TTC  AAC  ACG        864
His  Asn  Lys  Met  Val  Tyr  Phe  Ala  Ile  Ser  Asp  Tyr  Val  Phe  Asn  Thr
          250                     255                     260

GCC  AGC  CTG  GTT  TAT  CAT  GAG  GAA  GGA  TAT  CTG  AAC  TTC  TCC  ATC  ACA        912
Ala  Ser  Leu  Val  Tyr  His  Glu  Glu  Gly  Tyr  Leu  Asn  Phe  Ser  Ile  Thr
     265                     270                     275

GAT  GAG  ATG  ATA  CCG  CCT  GAC  TCT  AAT  ATC  CGA  CTG  ACC  ACC  AAG  TCC        960
Asp  Glu  Met  Ile  Pro  Pro  Asp  Ser  Asn  Ile  Arg  Leu  Thr  Thr  Lys  Ser
280                     285                     290                          295

TTC  CGA  CCC  TTC  GTC  CCA  CGG  TTA  GCC  AGG  CTC  TAC  CCC  AAC  ATG  AAC       1008
Phe  Arg  Pro  Phe  Val  Pro  Arg  Leu  Ala  Arg  Leu  Tyr  Pro  Asn  Met  Asn
                    300                     305                     310

CTG  GAA  CTC  CAG  GGA  TCA  GTG  CCC  TCT  GCT  CCG  CTC  CTG  AAC  TTC  AGC       1056
Leu  Glu  Leu  Gln  Gly  Ser  Val  Pro  Ser  Ala  Pro  Leu  Leu  Asn  Phe  Ser
               315                     320                     325

CCT  GGG  AAT  CTG  TCT  GTG  GAC  CCC  TAT  ATG  GAG  ATA  GAT  GCC  TTT  GTG       1104
Pro  Gly  Asn  Leu  Ser  Val  Asp  Pro  Tyr  Met  Glu  Ile  Asp  Ala  Phe  Val
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 330 |     |     |     |     | 335 |     |     |     |     | 340 |     |     |      |
| CTC | CTG | CCC | AGC | TCC | AGC | AAG | GAG | CCT | GTC | TTC | CGG | CTC | AGT | GTG | GCC | 1152 |
| Leu | Leu | Pro | Ser | Ser | Ser | Lys | Glu | Pro | Val | Phe | Arg | Leu | Ser | Val | Ala |      |
|     | 345 |     |     |     |     | 350 |     |     |     |     | 355 |     |     |     |     |      |
| ACT | AAT | GTG | TCC | GCC | ACC | TTG | ACC | TTC | AAT | ACC | AGC | AAG | ATC | ACT | GGG | 1200 |
| Thr | Asn | Val | Ser | Ala | Thr | Leu | Thr | Phe | Asn | Thr | Ser | Lys | Ile | Thr | Gly |      |
| 360 |     |     |     |     | 365 |     |     |     |     | 370 |     |     |     |     | 375 |      |
| TTC | CTG | AAG | CCA | GGA | AAG | GTA | AAA | GTG | GAA | CTG | AAA | GAA | TCC | AAA | GTT | 1248 |
| Phe | Leu | Lys | Pro | Gly | Lys | Val | Lys | Val | Glu | Leu | Lys | Glu | Ser | Lys | Val |      |
|     |     |     |     | 380 |     |     |     |     | 385 |     |     |     |     | 390 |     |      |
| GGA | CTA | TTC | AAT | GCA | GAG | CTG | TTG | GAA | GCG | CTC | CTC | AAC | TAT | TAC | ATC | 1296 |
| Gly | Leu | Phe | Asn | Ala | Glu | Leu | Leu | Glu | Ala | Leu | Leu | Asn | Tyr | Tyr | Ile |      |
|     |     |     | 395 |     |     |     |     | 400 |     |     |     |     | 405 |     |     |      |
| CTT | AAC | ACC | TTC | TAC | CCC | AAG | TTC | AAT | GAT | AAG | TTG | GCC | GAA | GGC | TTC | 1344 |
| Leu | Asn | Thr | Phe | Tyr | Pro | Lys | Phe | Asn | Asp | Lys | Leu | Ala | Glu | Gly | Phe |      |
|     |     | 410 |     |     |     |     | 415 |     |     |     |     | 420 |     |     |     |      |
| CCC | CTT | CCT | CTG | CTG | AAG | CGT | GTT | CAG | CTC | TAC | GAC | CTT | GGG | CTG | CAG | 1392 |
| Pro | Leu | Pro | Leu | Leu | Lys | Arg | Val | Gln | Leu | Tyr | Asp | Leu | Gly | Leu | Gln |      |
|     |     | 425 |     |     |     |     | 430 |     |     |     |     | 435 |     |     |     |      |
| ATC | CAT | AAG | GAC | TTC | CTG | TTC | TTG | GGT | GCC | AAT | GTC | CAA | TAC | ATG | AGA | 1440 |
| Ile | His | Lys | Asp | Phe | Leu | Phe | Leu | Gly | Ala | Asn | Val | Gln | Tyr | Met | Arg |      |
| 440 |     |     |     |     | 445 |     |     |     |     | 450 |     |     |     |     | 455 |      |
| GTT |     |     |     |     |     |     |     |     |     |     |     |     |     |     |     | 1443 |
| Val |     |     |     |     |     |     |     |     |     |     |     |     |     |     |     |      |

( 2 ) INFORMATION FOR SEQ ID NO:2:

( i ) SEQUENCE CHARACTERISTICS:
        ( A ) LENGTH: 481 amino acids
        ( B ) TYPE: amino acid
        ( D ) TOPOLOGY: linear ( i i ) MOLECULE TYPE: protein ( i x ) FEATURE:
        ( A ) NAME/KEY: misc_feature
        ( D ) OTHER INFORMATION: "rLBP"

( x i ) SEQUENCE DESCRIPTION: SEQ ID NO:2:

| Met | Gly | Ala | Leu | Ala | Arg | Ala | Leu | Pro | Ser | Ile | Leu | Leu | Ala | Leu | Leu |
|-----|-----|-----|-----|-----|-----|-----|-----|-----|-----|-----|-----|-----|-----|-----|-----|
| -25 |     |     |     | -20 |     |     |     |     | -15 |     |     |     |     |     | -10 |
| Leu | Thr | Ser | Thr | Pro | Glu | Ala | Leu | Gly | Ala | Asn | Pro | Gly | Leu | Val | Ala |
|     |     |     |     | -5  |     |     |     |     | 1   |     |     |     | 5   |     |     |
| Arg | Ile | Thr | Asp | Lys | Gly | Leu | Gln | Tyr | Ala | Ala | Gln | Glu | Gly | Leu | Leu |
|     |     | 10  |     |     |     |     | 15  |     |     |     |     | 20  |     |     |     |
| Ala | Leu | Gln | Ser | Glu | Leu | Leu | Arg | Ile | Thr | Leu | Pro | Asp | Phe | Thr | Gly |
|     |     | 25  |     |     |     |     | 30  |     |     |     |     | 35  |     |     |     |
| Asp | Leu | Arg | Ile | Pro | His | Val | Gly | Arg | Gly | Arg | Tyr | Glu | Phe | His | Ser |
| 40  |     |     |     |     | 45  |     |     |     |     | 50  |     |     |     |     | 55  |
| Leu | Asn | Ile | His | Ser | Cys | Glu | Leu | Leu | His | Ser | Ala | Leu | Arg | Pro | Val |
|     |     |     |     | 60  |     |     |     |     | 65  |     |     |     |     | 70  |     |
| Pro | Gly | Gln | Gly | Leu | Ser | Leu | Ser | Ile | Ser | Asp | Ser | Ser | Ile | Arg | Val |
|     |     |     |     | 75  |     |     |     |     | 80  |     |     |     |     | 85  |     |
| Gln | Gly | Arg | Trp | Lys | Val | Arg | Lys | Ser | Phe | Phe | Lys | Leu | Gln | Gly | Ser |
|     |     |     | 90  |     |     |     | 95  |     |     |     |     | 100 |     |     |     |
| Phe | Asp | Val | Ser | Val | Lys | Gly | Ile | Ser | Ile | Ser | Val | Asn | Leu | Leu | Leu |
|     |     | 105 |     |     |     |     | 110 |     |     |     |     | 115 |     |     |     |
| Gly | Ser | Glu | Ser | Ser | Gly | Arg | Pro | Thr | Val | Thr | Ala | Ser | Ser | Cys | Ser |
| 120 |     |     |     |     | 125 |     |     |     |     | 130 |     |     |     |     | 135 |
| Ser | Asp | Ile | Ala | Asp | Val | Glu | Val | Asp | Met | Ser | Gly | Asp | Leu | Gly | Trp |

|     |     |     |     | 140 |     |     |     |     | 145 |     |     |     |     | 150 |
|-----|-----|-----|-----|-----|-----|-----|-----|-----|-----|-----|-----|-----|-----|-----|

Leu Leu Asn Leu Phe His Asn Gln Ile Glu Ser Lys Phe Gln Lys Val
          155                 160             165

Leu Glu Ser Arg Ile Cys Glu Met Ile Gln Lys Ser Val Ser Ser Asp
          170                 175             180

Leu Gln Pro Tyr Leu Gln Thr Leu Pro Val Thr Thr Glu Ile Asp Ser
          185                 190             195

Phe Ala Asp Ile Asp Tyr Ser Leu Val Glu Ala Pro Arg Ala Thr Ala
200               205             210                         215

Gln Met Leu Glu Val Met Phe Lys Gly Glu Ile Phe His Arg Asn His
              220             225                     230

Arg Ser Pro Val Thr Leu Leu Ala Ala Val Met Ser Leu Pro Glu Glu
              235             240                 245

His Asn Lys Met Val Tyr Phe Ala Ile Ser Asp Tyr Val Phe Asn Thr
          250             255                 260

Ala Ser Leu Val Tyr His Glu Gly Tyr Leu Asn Phe Ser Ile Thr
          265             270                 275

Asp Glu Met Ile Pro Pro Asp Ser Asn Ile Arg Leu Thr Thr Lys Ser
280                     285                 290                 295

Phe Arg Pro Phe Val Pro Arg Leu Ala Arg Leu Tyr Pro Asn Met Asn
                  300                 305                 310

Leu Glu Leu Gln Gly Ser Val Pro Ser Ala Pro Leu Leu Asn Phe Ser
              315                 320                 325

Pro Gly Asn Leu Ser Val Asp Pro Tyr Met Glu Ile Asp Ala Phe Val
          330                 335                 340

Leu Leu Pro Ser Ser Ser Lys Glu Pro Val Phe Arg Leu Ser Val Ala
          345             350                 355

Thr Asn Val Ser Ala Thr Leu Thr Phe Asn Thr Ser Lys Ile Thr Gly
360                     365                 370                 375

Phe Leu Lys Pro Gly Lys Val Lys Val Glu Leu Lys Glu Ser Lys Val
                  380                 385                 390

Gly Leu Phe Asn Ala Glu Leu Leu Glu Ala Leu Leu Asn Tyr Tyr Ile
              395                 400                 405

Leu Asn Thr Phe Tyr Pro Lys Phe Asn Asp Lys Leu Ala Glu Gly Phe
          410                 415                 420

Pro Leu Pro Leu Leu Lys Arg Val Gln Leu Tyr Asp Leu Gly Leu Gln
425                     430                 435

Ile His Lys Asp Phe Leu Phe Leu Gly Ala Asn Val Gln Tyr Met Arg
440                 445                 450                 455

Val (2) INFORMATION FOR SEQ ID NO:3:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..591

(ix) FEATURE:
        (A) NAME/KEY: misc_feature
        (D) OTHER INFORMATION: "rLBP25"

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| GCC | AAC | CCC | GGC | TTG | GTC | GCC | AGG | ATC | ACC | GAC | AAG | GGA | CTG | CAG | TAT | 48 |
| Ala | Asn | Pro | Gly | Leu | Val | Ala | Arg | Ile | Thr | Asp | Lys | Gly | Leu | Gln | Tyr | |
| 1 | | | | 5 | | | | | 10 | | | | | 15 | | |
| GCG | GCC | CAG | GAG | GGG | CTA | TTG | GCT | CTG | CAG | AGT | GAG | CTG | CTC | AGG | ATC | 96 |
| Ala | Ala | Gln | Glu | Gly | Leu | Leu | Ala | Leu | Gln | Ser | Glu | Leu | Leu | Arg | Ile | |
| | | | 20 | | | | | 25 | | | | | 30 | | | |
| ACG | CTG | CCT | GAC | TTC | ACC | GGG | GAC | TTG | AGG | ATC | CCC | CAC | GTC | GGC | CGT | 144 |
| Thr | Leu | Pro | Asp | Phe | Thr | Gly | Asp | Leu | Arg | Ile | Pro | His | Val | Gly | Arg | |
| | | 35 | | | | | 40 | | | | | 45 | | | | |
| GGG | CGC | TAT | GAG | TTC | CAC | AGC | CTG | AAC | ATC | CAC | AGC | TGT | GAG | CTG | CTT | 192 |
| Gly | Arg | Tyr | Glu | Phe | His | Ser | Leu | Asn | Ile | His | Ser | Cys | Glu | Leu | Leu | |
| | 50 | | | | | 55 | | | | | 60 | | | | | |
| CAC | TCT | GCG | CTG | AGG | CCT | GTC | CCT | GGC | CAG | GGC | CTG | AGT | CTC | AGC | ATC | 240 |
| His | Ser | Ala | Leu | Arg | Pro | Val | Pro | Gly | Gln | Gly | Leu | Ser | Leu | Ser | Ile | |
| 65 | | | | | 70 | | | | | 75 | | | | | 80 | |
| TCC | GAC | TCC | TCC | ATC | CGG | GTC | CAG | GGC | AGG | TGG | AAG | GTG | CGC | AAG | TCA | 288 |
| Ser | Asp | Ser | Ser | Ile | Arg | Val | Gln | Gly | Arg | Trp | Lys | Val | Arg | Lys | Ser | |
| | | | | 85 | | | | | 90 | | | | | 95 | | |
| TTC | TTC | AAA | CTA | CAG | GGC | TCC | TTT | GAT | GTC | AGT | GTC | AAG | GGC | ATC | AGC | 336 |
| Phe | Phe | Lys | Leu | Gln | Gly | Ser | Phe | Asp | Val | Ser | Val | Lys | Gly | Ile | Ser | |
| | | | 100 | | | | | 105 | | | | | 110 | | | |
| ATT | TCG | GTC | AAC | CTC | CTG | TTG | GGC | AGC | GAG | TCC | TCC | GGG | AGG | CCC | ACA | 384 |
| Ile | Ser | Val | Asn | Leu | Leu | Leu | Gly | Ser | Glu | Ser | Ser | Gly | Arg | Pro | Thr | |
| | | 115 | | | | | 120 | | | | | 125 | | | | |
| GTT | ACT | GCC | TCC | AGC | TGC | AGC | AGT | GAC | ATC | GCT | GAC | GTG | GAG | GTG | GAC | 432 |
| Val | Thr | Ala | Ser | Ser | Cys | Ser | Ser | Asp | Ile | Ala | Asp | Val | Glu | Val | Asp | |
| | | 130 | | | | | 135 | | | | | 140 | | | | |
| ATG | TCG | GGA | GAC | TTG | GGG | TGG | CTG | TTG | AAC | CTC | TTC | CAC | AAC | CAG | ATT | 480 |
| Met | Ser | Gly | Asp | Leu | Gly | Trp | Leu | Leu | Asn | Leu | Phe | His | Asn | Gln | Ile | |
| 145 | | | | | 150 | | | | | 155 | | | | | 160 | |
| GAG | TCC | AAG | TTC | CAG | AAA | GTA | CTG | GAG | AGC | AGG | ATT | TGC | GAA | ATG | ATC | 528 |
| Glu | Ser | Lys | Phe | Gln | Lys | Val | Leu | Glu | Ser | Arg | Ile | Cys | Glu | Met | Ile | |
| | | | | 165 | | | | | 170 | | | | | 175 | | |
| CAG | AAA | TCG | GTG | TCC | TCC | GAT | CTA | CAG | CCT | TAT | CTC | CAA | ACT | CTG | CCA | 576 |
| Gln | Lys | Ser | Val | Ser | Ser | Asp | Leu | Gln | Pro | Tyr | Leu | Gln | Thr | Leu | Pro | |
| | | | 180 | | | | | 185 | | | | | 190 | | | |
| GTT | ACA | ACA | GAG | ATT | | | | | | | | | | | | 591 |
| Val | Thr | Thr | Glu | Ile | | | | | | | | | | | | |
| | | | | 195 | | | | | | | | | | | | |

( 2 ) INFORMATION FOR SEQ ID NO:4:

( i ) SEQUENCE CHARACTERISTICS:
        ( A ) LENGTH: 197 amino acids
        ( B ) TYPE: amino acid
        ( D ) TOPOLOGY: linear ( i i i ) MOLECULE TYPE: protein ( i x ) FEATURE:
        ( A ) NAME/KEY: misc_feature
        ( D ) OTHER INFORMATION: "rLBP25"

( x i ) SEQUENCE DESCRIPTION: SEQ ID NO:4:

| | | | | | | | | | | | | | | | |
|---|---|---|---|---|---|---|---|---|---|---|---|---|---|---|---|
| Ala | Asn | Pro | Gly | Leu | Val | Ala | Arg | Ile | Thr | Asp | Lys | Gly | Leu | Gln | Tyr |
| 1 | | | | 5 | | | | | 10 | | | | | 15 | |
| Ala | Ala | Gln | Glu | Gly | Leu | Leu | Ala | Leu | Gln | Ser | Glu | Leu | Leu | Arg | Ile |
| | | | 20 | | | | | 25 | | | | | 30 | | |
| Thr | Leu | Pro | Asp | Phe | Thr | Gly | Asp | Leu | Arg | Ile | Pro | His | Val | Gly | Arg |
| | | 35 | | | | | 40 | | | | | 45 | | | |
| Gly | Arg | Tyr | Glu | Phe | His | Ser | Leu | Asn | Ile | His | Ser | Cys | Glu | Leu | Leu |

-continued

|  |  |  |  |  | 50 |  |  |  | 55 |  |  |  |  | 60 |  |
|--|--|--|--|--|--|--|--|--|--|--|--|--|--|--|--|
| His 65 | Ser | Ala | Leu | Arg | Pro 70 | Val | Pro | Gln | Gly 75 | Leu | Ser | Leu | Ser | Ile 80 |
| Ser | Asp | Ser | Ser | Ile 85 | Arg | Val | Gln | Gly | Arg 90 | Trp | Lys | Val | Arg | Lys 95 | Ser |
| Phe | Phe | Lys | Leu 100 | Gln | Gly | Ser | Phe | Asp 105 | Val | Ser | Val | Lys | Gly 110 | Ile | Ser |
| Ile | Ser | Val 115 | Asn | Leu | Leu | Leu | Gly 120 | Ser | Glu | Ser | Ser | Gly 125 | Arg | Pro | Thr |
| Val | Thr 130 | Ala | Ser | Ser | Cys | Ser 135 | Ser | Asp | Ile | Ala | Asp 140 | Val | Glu | Val | Asp |
| Met 145 | Ser | Gly | Asp | Leu | Gly 150 | Trp | Leu | Leu | Asn | Leu 155 | Phe | His | Asn | Gln | Ile 160 |
| Glu | Ser | Lys | Phe | Gln 165 | Lys | Val | Leu | Glu | Ser 170 | Arg | Ile | Cys | Glu | Met 175 | Ile |
| Gln | Lys | Ser | Val 180 | Ser | Ser | Asp | Leu | Gln 185 | Pro | Tyr | Leu | Gln | Thr 190 | Leu | Pro |
| Val | Thr | Thr | Glu 195 | Ile |